United States Patent [19]
Larsson et al.

[11] Patent Number: 5,906,831
[45] Date of Patent: *May 25, 1999

[54] CONTROLLED RELEASE COMPOSITION FORMING A REVERSED MICELLAR (L2) STRUCTURE OR A NORMAL MICELLAR (L1) STRUCTURE

[75] Inventors: Kåre Larsson, Bjärred; Helena Ljusberg-Wahren, Höllviken, both of Sweden

[73] Assignee: GS Development AB, Malmo, Sweden

[ * ] Notice: This patent issued on a continued prosecution application filed under 37 CFR 1.53(d), and is subject to the twenty year patent term provisions of 35 U.S.C. 154(a)(2).

[21] Appl. No.: 08/836,103
[22] PCT Filed: Dec. 8, 1995
[86] PCT No.: PCT/SE95/01479
§ 371 Date: Apr. 29, 1997
§ 102(e) Date: Apr. 29, 1997
[87] PCT Pub. No.: WO96/17597
PCT Pub. Date: Jun. 13, 1997

[30] Foreign Application Priority Data

Sep. 12, 1994 [SE] Sweden .................................. 9404289

[51] Int. Cl.$^6$ .............................. A61K 9/127; A61K 9/10
[52] U.S. Cl. ........................... 424/450; 424/400; 424/43; 424/45; 428/402.2; 514/937
[58] Field of Search .................................. 424/450, 1.21, 424/9.321, 9.51, 417, 400, 43–45; 436/829; 428/402.2; 514/937–943

[56] References Cited

U.S. PATENT DOCUMENTS 5,151,272   9/1992   Engstrom et al. ....................... 424/450

FOREIGN PATENT DOCUMENTS 0 314 689   4/1992   European Pat. Off. .

OTHER PUBLICATIONS

Larsson, Kåre, "The Structure of Mesomorphic Phases and Micelles in Aqueous Glyceride Systems", *Z. Phys. Chem.* 56 (1967), pp. 173–198.

Johnson, Keith, et al., "Controlled Release of Steroids Through Microporous Membranes with Sodium Dodecyl Sulfate Micelles", *Pharmaceutical Research*, vol. 6, No. 3, 1989, pp. 239–243.

Hills, Brian A., *The Biology of Surfactant*, Cambridge University Press, (1988).

"Surface Behavior of Adsorbed Films from Protein–Amphiphile Mixtures", *Progress in Colloid & Polymer Science*, vol. 70, B. Ericsson et al., pp. 92–95, 1985.

*Primary Examiner*—Gollamudi S. Kishore
*Attorney, Agent, or Firm*—Burns, Doane, Swecker & Mathis, L.L.P.

[57] ABSTRACT

A controlled-release composition for a biologically active material, characterized in that it comprises a mixture of: a) monocaproin, optionally in admixture with moncaprylin and/or monocaprin, and b) a polar liquid selected from the group consisting of such polar liquids which are capable of forming an L2 phase with a), and c) a biologically active material dissolved or dispersed in said mixture of a) and b), a) being present in the composition, based on the total weight of a)+b), in an amount of from the lower limit where the mixture of a) and b) forms a reversed micellar (L2) structure and up to 100% by weight of a), with the further proviso that said mixture of a) and b) is essentially within that specific domain of the L2 structure, in a phase diagram, where said L2 structure will change to a normal micellar (L1) structure if contacted with an external polar liquid. Said composition is preferably used as a medial composition.

35 Claims, 1 Drawing Sheet

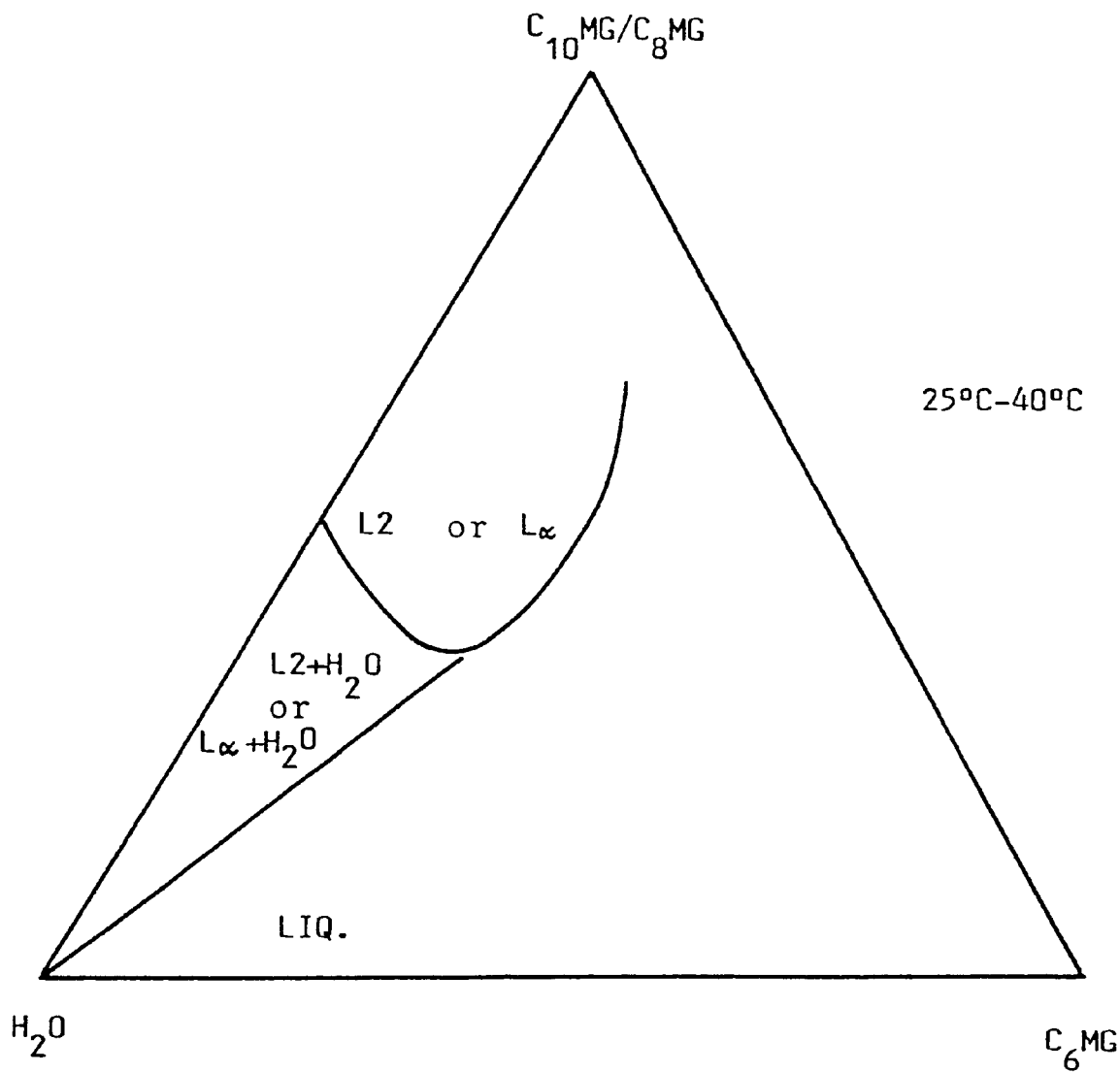

CONTROLLED RELEASE COMPOSITION FORMING A REVERSED MICELLAR (L2) STRUCTURE OR A NORMAL MICELLAR (L1) STRUCTURE

This application is 371 of PCT/SE95/01479 filed Dec. 8, 1995.

TECHNICAL FIELD the present invention is within the field of encapsulating biologically active materials in order to obtain a controlled, or sustained, release thereof as is desirable within many different technical fields, such as for instance to have a longer lasting or delayed effect of a pharmaceutically active material. More specifically the invention is based on a novel encapsulating or carrier material or system which enables a highly reproducible sustained release (reduced biological variability) of biologically active compounds. With reference to last-mentioned property the term "controlled release" will be generally used throughout description and claims to emphasize the fact that by the present invention the desired sustained release of the active compound can be obtained in a controlled way.

BACKGROUND OF THE INVENTION

About thirty years ago one of the inventors, K. Larsson, in Z. phys. Chem. 56 (1967), 173, reported that the aqueous system of monocaproin, which is a lipid the complete name of which is glycerolmonohexanoate or glycerolmonocapronate, forms one single liquid phase at all compositions. At that time this was a unique and remarkable behaviour of a single amphiphilic (surfactant) molecule; only mixtures of surfactants and cosurfactants were known to exceptionally show such lack of a phase transition when the composition was changed from anhydrous towards pure water.

Recent work within the field of drug delivery, with special regard to molecules that need to be protected against enzymatic degradation (like peptides), has shown that so called microemulsions or L2-phases provide a useful carrier system. An example of such an L2-system is disclosed in European patent specification No. 314 689, which discloses the utilization of $C_{16-22}$-monoglycerides interacting with $C_{16-22}$-triglycerides and a polar liquid.

although the phase properties of monocaproin have been known for a very long time, however, it has not been realized earlier that this unusual micellar phase can provide a highly efficient carrier in connection with for instance drug delivery, as far as is known to applicant. The main reason probably is that a molecule with such a short hydrocarbon chain is regarded more as an organic solvent than as a lipid and has, therefore, not been expected to provide efficient solubilization power of drugs into an association-colloid type of structure.

When amphiphilic systems forming ordinary micellar solutions (L1-solution) have been used in drug delivery, relatively long hydrocarbon chains have also been involved; cf. K. A. Johnson, G. B. Westermann-Clark, and D. Shaf, Pharmaceut. Res. 6 (1989), 239.

Furthermore, it can be added that Ericsson and Hegg in Progr. Colloid & Polymer Sci. 70 (1985), 92, have reported a study of the surfactant behaviour of 1-monocaproin and its interaction with ovalbumin in a diluted water solution. The critical micellar concentration (cmc) of monocaproin was found to be 160 mM. Their result demonstrated that there is no molecular interaction between this specific protein and monocaproin. We have now unexpectedly found that the micellar system according to the present invention exhibits full compatibility with any protein also at high concentrations, i.e. even up to and including the region where the L1-type of structure changes to the L2-type of structure.

GENERAL DESCRIPTION OF THE INVENTION

Thus the present invention is based on the unexpected finding that monocaproin is highly efficient in solubilizing amphiphilic biologically active materials, especially drug molecules, and that the successive change from an L2-type of micellar solution into an L1-type thereof without any phase separation provides a useful mechanism for protecting molecules which are sensitive to enzymatic degradation, and also for sustained release, particularly in drug administration, for instance oral administration.

It has also been found that lipase degradation of the new compositions according to the present invention is extremely slow compared to previously disclosed glyceride-based formulations. As is realized by a person skilled in the art this is a very significant factor in especially oral drug carrier systems.

A pronounced problem in the oral delivery of drugs by lipid-based formulations is furthermore the interference between the lipids of the drug formulation and the lipids in foods. In order to accomplish a reproducible drug uptake it is therefore advisable and sometimes even necessary to take the drug on an empty stomach, which may of course be disadvantageous. Fats and oils in foods are often covered by a surface layer of amphiphilic molecules, usually polar lipids, and these surface lipids and the dominating core of oils/fats are always in an emulsified state in the gastrointestinal tract. A general complication in connection with previously known drug delivery systems based on lipids is that these emulsions originating from the food will interact with the drug carrier system, which means that the food composition can influence upon the drug uptake.

A most remarkable and unexpected property of monocaproin, contrary to previously described lipid systems, is that the aqueous phase thereof does not solubilize triglyceride oils or fats, and not even so called medium chain triglycerides or pure tricaprylin.

An addition factor to consider in oral administration of drugs is the phospholipid surface layer covering the gastric and the intestinal mucous layer; cf. B. A. Hills, The Biology of Surfactant, Cambridge University Press, Cambridge, (1988). the new micellar composition according to the present invention has such a small interaction with these phospholipids that said interaction can be neglected in a corresponding drug carrying system, which is contrary to the situation in connection with the previously known lipid drug carriers.

More specifically, according to the first aspect of the invention, there is accomplished a new controlled-release composition for a biologically active material, which composition is characterized in that it comprises a mixture of:
a) monocaproin, optionally in admixture with a monoglyceride selected from the group consisting of $C_6$–$C_{10}$-fatty acid monoglycerides, i.e. monocaprylin and/or monocaprin, and
b) a polar liquid selected from the group consisting of such polar liquids which are capable of forming an L2 phase with a), and
c) a biologically active material dissolved or dispersed in said mixture of a) and b), a) being present in the composition, based on the total weight of a)+b), in an amount of from the lower limit where the mixture of a) and b) forms a reversed micellar (L2) structure and up to 100% by weight of a), with the proviso that said mixture of a) and b) is also essentially within that specific domain of the L2 structure, in a phase diagram, where said L2 structure will change to a normal micellar (L1) structure if contacted with an external polar liquid.

Thus, if firstly considering the binary system monocaproin-water said system shows micellar molecular assemblies at all concentrations in the temperature range between about room temperature and about 100° C., with an inverted L2-type of structure, which continuously goes over to an ordinary micellar solution (L1) when raising the proportion of water. These two micellar phases are highly efficient solubilizers of lipophilic materials and the continuous phase change L2→L1 has been shown to give an outstanding sustained or controlled release of the lipophilic substance, as well as the additional advantages referred to above.

With reference to the specific embodiment where a binary system of monocaproin and water is utilized it should be emphasized that the invention is applicable also up to the extreme end with 100% of monocaproin, i.e. the invention also covers the case where there is in fact no water or other polar liquid present at the beginning. This is an important advantage contrary to earlier known aqueous formulations as ordinary capsules do not allow water.

As concerns the statement that the mixture of a) and b) is also "essentially" within that specific domain of the L2-structure where a change to an L1-structure only is accomplished in contact with an external polar liquid, this means that it may be borderline cases where a specific application permits the presence of a second phase, e.g. $L_\alpha$, in a minor or negligible amount. No specific figure can be given here, but that aspect is easily considered by a person skilled in the art from case to case.

A very important feature in connection with the release or delivery applications in accordance with the invention also is that we have found that water can be replaced with any other polar liquid that is capable of forming the L2-phase referred to in connection with the invention. Thus, it has been found that also with other polar liquids the same type of association-colloid structures exist with said continous phase change from L2 to L1.

In the case of low solubility of a desired biologically active material it has been found that the solubilization can be increased by the addition of $C_8$–$C_{10}$-fatty acid monoglycerides, provided that said addition is made in such a way that it does not influence upon the uniqe one-phase behaviour. Thus, the addition has to be kept within that specific part of the L2-domaine which, when contacted with water or any other polar liquid from the surroundings e.g. the intestin or the stomach, will cause the desired continous phase change from L2 to L1. The specific composition to be used in each separate case is easily determined by a person skilled in the art by using a phase diagram, as will be illustrated further below in connection with the figure.

In connection with the general inventive idea it could also be added that in principle the $C_4$-monoglyceride, i.e. monobutyrin, can be expected to act in a way similar to that of monocaproin. However, in practice it does not seem to be any realistic alternative, inter alia for such reasons as being instable and having an unpleasant taste and smell.

With reference to preferable embodiments of the composition according to the invention the following ones can be referred to.

As concerns the optional presence of said $C_8$–$C_{10}$-fatty acid glyceride the difference in the effect of added monocaprin as compared to monocaprylin is quite small when considering the extent of the one-phase region used in the present invention. A slightly higher ratio of said long-chain monoglyceride/monocaproin is possible without the occurence of a second phase when using monocaprylin as compared to monocaprin. Another difference that may be referred to in this connection is that the second phase occuring in these systems, which is the lamellar liquid-crystalline phase $L_\alpha$ at 25–25° C., melts into a separate L2-phase in the monocaprylin system when the temperature is increased towards 40° C.

Apart from using the pure compounds monocaprylin and/or monocaprin said optional ingredients of the composition according to the invention may also be used in the form of a technical monoglyceride mixture prepared from so called medium chain triglycerides, which mixture should give an intermediate behaviour as compared to that of monocaprin or monocaprylin descried above.

The polar liquid used as ingredient b) of the composition according to the invention is preferably selected from the group consisting of water, glycerol, ethylene glycol and propylene glycol. Another useful polar liquid is a lower alkanol such as ethanol.

As concerns the external polar liquid referred to in connection with the change from an L2-structure into an L1-structure said liquid generally is gastric juice or other body fluid in connection with the drug aspect of the invention, but as the invention is not strictly limited to a controlled release of drugs only, said polar liquid may also well be any of the polar liquids referred to above. Thus, said external polar liquid is also preferably water, glycerol, ethylene glycol or propylene glycol, also in connection with non-medical uses of the composition claimed, where sustained release of a biologically active ingredient is desired.

The biologically active material is generally selected from the group consisting of amphiphilic and lipophilic materials and preferably pharmaceutical lipophilic compounds. Examples of such pharmaceutical compounds in connection with which the invention is especially preferable are antibiotics, proteins, peptides, steroids, vitamins, nucleic acids and vaccines.

An especially interesting biological active compound is a protein or a peptide, preferably cyclosporin, desmopressin (dDAVP) or vasopressin or calcitonins. A highly preferable use of said cyclosporin in connection with the invention is as an immunosuppresive drug.

As has been described above ingredient a) of the composition claimed can be present up to 100% by weight, based on the total weight of a)+b). Generally this means that a) is present within the range of 50–100% by weight, more preferably 80–100% by weight.

The biologically active material is preferably present in the composition according to the invention in an amount of 0.1–20, more preferably 0.2–12, % by weight based on the total weight of a)+b).

Lipases in saliva, in gastric mucosa and of course the strongly dominating pancreatic lipase degrade lipids in oral drug delivery systems based on lipids. It is well known that lipases also attack other lipids than triglycerides, for example phospholipids, galactolipids, diglycerides and monoglycerides (the 1-isomer). A requirement for the enzymatic degradation (to take place with a reasonable velocity) is the existence of an interphase between water and the actual lipid phase where the lipase is localized. An interesting feature of our new composition or system is the lack of such an interphase. This means that the protection of substances in the gastrointestinal system is much more effective than in lipid systems forming separate phases which are coexisting with an aqueous phase. This property must be considered of outmost importance in protecting peptides in oral delivery.

In order to increase the life-time of the monocaproin micelles in the intestinal system the addition of minor amounts of food emulsifiers can be used to improve the protection of the drug against the intestinal enzymes. Therefore, another preferable embodiment of the invention is represented by a composition which contains a food emulsifier, preferably an emulsifier which contains a polyoxyethylene chain.

Still another preferable embodiment of the invention is a composition wherein said monocaproin comprises either the 1-isomer or the 2-isomer, i.e. where the monocaproin is essentially pure 1-monocaproin or essentially pure 2-monocaproin.

Since, the invention is of special importance in connection with drug delivery another aspect of the invention is represented by a composition as previously defined for use as a medical composition, i.e. primarily for the controlled release of a biologically active material in the form of a drug or medical compound.

Preferable embodiments of such a composition are those embodiment which have already been disclosed in connection with the controlled-released composition per se. Thus, they will not be repeated here.

In connection with the medical composition it should, however, be added that it is preferably adapted for oral delivery of the drug. Such an embodiment is especially interesting in connection with proteins, since proteins in aqueous solution have a tendency to unfold at the air-water interphase, but when monocaproin is present above CMC (critical micell concentration), it will squeeze out the proteins from the air/water interphase. Such a drug delivery system therefore also has a protective effect on protein stability.

If the protein, or other medical substance is unstable in an aqueous solution the present invention is preferably utilized with propylene glycol or glycerol as said polar liquid because such a system is more stable than a water-monocaproin system. Thus, as glycerol-monocaproin form the same type of association colloids as water-monocaproin, the former system is preferred in oral delivery of such proteins.

Furthermore, the finding that monocaproin can reduce the interfacial tension without solubilizing usual lipids means that it can increase the penetration through the skin without destroying the physiologically important lipid barrier on stratum corneum. Drug delivery by the micellar system according to the present invention through the skin therefore represents an application particularly well suited to situations when fast and efficient drug penetration is desired. That is, still another preferably embodiment of the medical composition claimed is a composition which has been adapted for transdermal delivery of the drug.

According to still another aspect of the invention it can be defined as the use of a composition as defined above for the manufacture of a medicament comprising a protein or a peptide as the active medical compound and adapted for oral or transdermal administration of said medical compound.

An especially interesting medical compound in this context is clyclosporin, primarily for use as an immunosuppresive drug.

For biologically active non-medical materials the invention can also be defined as the use of a composition as defined above for the controlled release of said non-medical material.

An example of such a non-medical material is an enzyme for a biotechnology application, but various other materials and applications are of course possible within the scope of the invention as is realized by a person skilled in the art.

The invention also relates to a method of preparing the controlled-release composition defined, which method generally comprises mixing a) and b) so as to form an L2-structure as defined and dissolving or dispersing c) therein during or after said mixing of a) and b) so as to obtain said controlled-release composition.

This general method of preparing the composition should cause the skilled artisan no problem and further details in this context should not be needed here.

However, it could be added that in a case where there may be an interaction between the biologically active material and ingredient a) of the composition, a preferable embodiment of the method comprises forming said L2-structure of a) and b) and keeping it separate from c) up to the moment of use, preferably in a two-compartment delivery system, and then dissolving or dispersing c) in said L2-structure when the controlled-release composition is to be utilized.

Finally, another aspect of the invention, which is also based on the finding of the outstanding properties of monocaproin as a carrier for a protein or a peptide, is represented by a composition for use as a nasal medical composition, which is characterized in that it comprises a protein or peptide included in an spray delivery composition comprising a mixture of a) monocaproin, optionally in admixture with monocaprylin and/or monocaprin, and
b) a polar liquid, which is preferably selected from the group consisting of water, glycerol, ethylene glycol and propylene glycol, a) and b) being present in the composition in such a mutual ratio that they form a micellar structure in an aerosol form.

Thus, according to this aspect of the invention a) can be present in such a small amount only that a normal micellar (L1)structure is at hand already from the beginning in said nasal composition. In other words the protein or peptide may in fact be ready for delivery or release already in the spray composition. However, this spray delivery aspect of the composition works also up in the micellar L2-structure range. Generally this means that a) can be present in such a spray delivery composition in an amount of about 2–70, preferably 2–50, more preferably 2–20% by weight, based on the total weight of a)+b).

Said aerosol composition for use as a nasal medical composition preferably comprises or essentially consists of insulin as said protein or peptide.

Another way of expressing the invention is by a method of administering to a mammal, especially man, a biologically active material, which method comprises providing a composition as defined above and administering an effective amount thereof to the body of said mammal, whereby a controlled release of said composition is obtained.

A BRIEF DESCRIPTION OF THE DRAWING

The figure schematically shows a ternary system of monocaproin ($C_6$MG)/$H_2O$/monocaprylin ($C_8$MG) or monocaprin-($C_{10}$MG) at 25° C.–40° C.

The term "LIQ" is used to show those regions where one single phase in the form of L2 or L1 exists. Another phase occurring in the system shown is the lamellar liquid-crystalline phase $L_\alpha$ and the expressions $L2+H_2O$ and $L_\alpha+H_2O$ indicate two-phase regions, through which one can not essentially pass if utilizing the inventive idea. Thus, to obtain the desired effects according to the invention one should start within that area of the LIQ-region where the addition of water means a continuous structure change from L2 to L1.

As was said above this figure is a schematic figure only, and in a specific case the exact information needed for performing the invention can be taken from the specific phase diagram referred to.

EXAMPLES

Example 1

86 mg of cyclosporin A was dissolved in 860 mg of monocaproin. To the solution 20 g of water was added.

Microscopic inspection of the sample in polarized light showed no birefringence. This shows that the cyclosporin has been dissolved in the monocaproin phase.

Example 2

Cyclosporin in an amount of 9 g was dissolved in 91 g of monocaproin. The solution obtained was transferred to 100 mg gelatin capsules covered by a solid fat film acting as a protection during the passage of the capsule through the gastric region.

Example 3

A solution was prepared from 30 g of monocaprin in 60 g of monocaproin. This solution was added to a heparin-solution containing 10 000 IE/ml. This preparation for oral heparin delivery is supplied via the same kind of capsules as in example 2.

Example 4

The human insulin preparation Insulatard from Novo Nordisk with 100 IE/ml was converted to a preparation for nasal delivery as a spray merely by adding monocaproin in a concentration of 4% (w/w).

Example 5

A homogenous sample was prepared by mixing an aqueous solution of the peptide dDAVP (desmopressin) (1070 µg/ml) with monocaproin (monohexanoin from Larodan, Malmö, Sweden) in the weight ratio of 1 to 9, to give a final concentration of 107 µg/ml. 1 mg/kg bodyweight of this solution was fed intragastrically to eight rats, as was a corresponding saline solution of dDAVP.

The bioavailabiliyt of dDAVP was 2.0% from the monocaproin containing solution and 0.2% from the saline solution.

Thus, what can be seen from this Example is a drastic increase of the bioavailability of the peptide by the composition according to the invention.

Example 6

Many galenic formulations of drugs contain polar solvents. In order to demonstrate the excellent miscibility of monocaproin with polar solvents, the following mixtures were prepared and inspected visually. The Table below shows the results. The clear, low viscous appearance confirms that it is a solution.

TABLE

| Polar solvent | % (w/w) Polar solvent | % Monocaproin | Appearance |
| --- | --- | --- | --- |
| Ethanol | 10 | 90 | clear, low viscous |
| Propylene Glycol | 10 | 90 | clear, low viscous |
| Ethanol/ Propylene Glycol | 5 5 | 90 | clear, low viscous |
| Ethanol | 90 | 10 | clear, low viscous |

We claim:

1. A controlled-release composition for a biologically active material, comprising:
    a) monocaproin, optionally in admixture with monocaprylin or monocaprin or a mixture thereof, or
    a) in admixture with b) a polar liquid selected from the group consisting of such polar liquids which are capable of forming an L2 phase with a) and
    c) a biologically active material dissolved or dispersed in a) or said mixture of a) and b), a) being present in the composition in such an amount where a) or said mixture of a) and b) forms a reversed micellar (L2) structure up to 100% by weight of a) based on the total weight of a)+b), with the proviso that said mixture of a) and b) is also essentially within that specific domain of the L2 structure, in a phase diagram, where said L2 structure will change to a normal micellar (L1) structure if contacted with an external polar liquid, the composition releasing said active material via a successive change from L2 structure into L1 structure without any phase separation when contacted with said external polar liquid.

2. A composition according to claim 1, wherein said monocaprylin or monocaprin or mixture thereof is present in the form of a mixture obtained from $C_8$–$C_{10}$-fatty acid triglycerides.

3. A composition according to claim 1, characterized in that said polar liquid is selected from the group consisting of water, glycerol, ethylene glycol and propylene glycol.

4. A composition according to claim 1, wherein the biologically active material is selected from the group consisting of amphiphilic and lipophilic materials.

5. A composition according to claim 4, wherein said biologically active material is a protein or a peptide.

6. A composition according to claim 1, wherein a) is present in the composition, based on the total weight of a)+b), in an amount of 50–100% by weight.

7. A composition according to claim 1, wherein the biologically active material c) is present in an amount of 0.1–20% by weight, based on the total weight of a)+b).

8. A composition according to claim 1, further comprising a food emulsifier.

9. A composition according to claim 1, characterized in that said monocaproin comprises pure 1-monocaproin or pure 2-monocaproin.

10. A composition as defined in claim 1 for use as a medicament for the controlled release of a biologically active material in the form of a pharmaceutical compound.

11. A composition according to claim 10 which has been adapted for oral delivery of said pharmaceutical compound.

12. A composition according to claim 11, characterized in that said polar liquid is propylene glycol or glycerol.

13. A composition according to claim 10, characterized in that it has been adapted for transdermal delivery of said pharmaceutical compound.

14. A method for manufacturing a medicament comprising incorporating into the composition as defined in claim 1 a protein or a peptide as an active pharmaceutical compound and adapted for oral or topical administration of said pharmaceutical compound.

15. A method for manufacturing according to claim 14 wherein said medicament comprises cyclosporin as an immunosuppressive drug.

16. A method for the controlled release of a biologically active non-medical material comprising administering the composition of claim 1 including said biologically active non-medical material to a mammal and obtaining a controlled release of said composition.

17. A method for the controlled release of a biologically active non-medical material according to claim 16, wherein said non-medical material is an enzyme.

18. A method of preparing a controlled-release composition according to claim 1, characterized by mixing a) and b) so as to form an L2-structure as defined and dissolving or dispersing c) therein during or after said mixing of a) and b) so as to obtain said controlled-release composition.

19. A method according to claim 18, characterized by forming said L2-structure of a) and b) and keeping it separate from c) up to the moment of use, preferably in a two-compartment delivery system, and then dissolving or dispersing c) in said L2-structure when the controlled-release composition is to be utilized.

20. A composition for use as a nasal medical composition, comprising a protein or peptide in a spray delivery composition comprising a mixture of a) monocaproin, optionally in admixture with monocaprylin or monocaprin or a mixture thereof, and b) a polar liquid, which is preferably selected from the group consisting of water, glycerol, ethylene glycol, and propylene glycol, a) and b) being present in the composition in such a mutual ratio that they form a micellar structure in an aerosol form.

21. A composition according to claim 20, wherein a) is present in said composition in an amount of about 2–70% by weight, based on the total weight of a)+b).

22. A composition according to claim 20, characterized in that said protein or peptide comprises insulin.

23. A method of administering to a mammal, especially man, a biologically active material, characterized by providing a composition as defined in claim 1 and administering an effective amount thereof to the body of said mammal, whereby a controlled release of said composition is obtained.

24. A composition according to claim 21, characterized in that said protein or peptide comprises insulin.

25. A composition according to claim 4, wherein said amphiphilic and lipophilic materials are pharmaceutical compounds.

26. A composition according to claim 25, wherein said pharmaceutical compounds are antibiotics, proteins, peptides, steroids, vitamins, nucleic acids or vaccines.

27. A composition according to claim 5, wherein said protein or peptide is cyclosporin, desmopressin, vasopressin or a calcitonin.

28. A composition according to claim 6, wherein a) is present in an amount of 80–100% by weight.

29. A composition according to claim 7, wherein the biologically active material c) is present in an amount of 0.2–10% by weight.

30. A composition according to claim 8, wherein said food emulsifier contains a polyoxyethylene chain.

31. A composition according to claim 11, wherein said pharmaceutical compound is a protein.

32. A composition according to claim 21, wherein a) is present in an amount of about 2–50% by weight.

33. A composition according to claim 32, wherein a) is present in an amount of about 2–20% by weight.

34. A composition according to claim 1, wherein said polar liquid is a lower alkanol.

35. A composition according to claim 34, wherein said lower alkanol is ethanol.

* * * * *